United States Patent [19]

Christoffersen et al.

[11] 4,319,491

[45] Mar. 16, 1982

[54] METHOD AND APPARATUS FOR DETERMINING AT LEAST ONE COMPONENT OF A SAMPLE OF GRAIN, SEED, OR ANOTHER PARTICULATE MATERIAL

[75] Inventors: Sten R. Christoffersen, Hillerod; Johan C. Gregersen, Soborg; Mogens B. Larsen, Helsinge, all of Denmark

[73] Assignee: A/S N. Foss Electric, Hillerod, Denmark

[21] Appl. No.: 46,709

[22] Filed: Jun. 8, 1979

[30] Foreign Application Priority Data

Jun. 9, 1978 [DK] Denmark .............................. 2599/78
Dec. 27, 1978 [FR] France ................................ 78 36446

[51] Int. Cl.³ ............................................. G01R 27/26
[52] U.S. Cl. .................................... 73/662; 324/61 R
[58] Field of Search ......................... 73/662, 571, 579; 324/61 R; 141/71, 83, 74, 80, 12

[56] References Cited

U.S. PATENT DOCUMENTS

| | | | |
|---|---|---|---|
| 2,353,492 | 7/1944 | O'Connor | 141/74 |
| 2,523,363 | 9/1950 | Gehman | 324/61 R |
| 2,665,409 | 1/1954 | Rogers | 324/61 R |
| 3,739,264 | 6/1973 | Resh | 324/61 R |
| 4,121,151 | 10/1978 | Funk et al. | 324/61 R |

*Primary Examiner*—Stephen A. Kreitman
*Attorney, Agent, or Firm*—Dennison, Meserole, Pollack & Scheiner

[57] ABSTRACT

A method and apparatus for determining at least one component of a sample of a particulate material, such as grain or seed, on the basis of a permittivity value of the sample. Before measuring the permittivity value the sample is compacted to a predetermined degree, preferably by vibrating the sample. Preferably, the sample is vibrated while being introduced into a sample container or receptacle in which the sample is exposed to an alternating electric field for determining said permittivity value.

2 Claims, 2 Drawing Figures

METHOD AND APPARATUS FOR DETERMINING AT LEAST ONE COMPONENT OF A SAMPLE OF GRAIN, SEED, OR ANOTHER PARTICULATE MATERIAL

BACKGROUND OF THE INVENTION

1. Field of the invention

The present invention relates to a method and an apparatus for determining at least one component of a sample of grain, seed or another particulate material which is arranged in a sample container or receptacle and exposed to an alternating electric field, while a permittivity value of said sample is being measured for determining said component on the basis of that value.

2. Description of the Prior Art

In the past, the dielectric properties of grain, seed, and other organic materials have been subject to thorough theoretical and practical analyses. Thus, it is well known that the dielectric constant or permittivity of a water-containing sample arranged in an alternating electric field is correlated with the water content of the sample. This correlation is primarily due to the fact that the water molecules possess a static electric dipole moment. Consequently, the dielectric constant or permittivity of a water-containing sample arranged in an alternating electric field will be dependent on the number of water molecules in the sample. Not only the water molecules, but also possible protein molecules and molecules of other components of the sample being measured may contribute to the dielectric constant or the permittivity of the sample by possessing static or induced dipole moments. Therefore, it has been proposed to determine also other components than water on the basis of permittivity measurements of a sample.

SUMMARY OF THE INVENTION

The present invention relates to such measurements including determination of the dielectric constant or permittivity of a sample and has for its object to make these measurements more accurate and reliable than hitherto possible.

Thus the present invention provides a method of determining at least one component of a sample of a particulate material, such as grain or seed, said method comprising arranging said sample in a container or receptacle, compacting said sample in said container or receptacle to a predetermined degree, exposing said compacted sample in said container or receptacle to an alternating electric field, measuring a permittivity value of said compacted sample, and determining said component on the basis of said permittivity value.

It has been found that the permittivity of a grain-like or particulate material is not only dependent on the components of the material, but also on the degree to which the particles of the material in the sample are compacted or packed together. Consequently, in order to obtain reliable measurements it is important that the particles of like samples the measurements of which are to be compared, are compacted in the sample receiving container to substantially the same degree. When a sample of particulate material is compacted before measurement, a result of the measurement will be less sensitive to or dependent on accidental vibrations or shocks during measurements.

According to the invention the sample is preferably compacted by imparting a vibrational movement to the sample receiving container or receptacle. The vibration of the sample may be initiated when the total sample has been placed in the sample receiving container or receptacle. It has been found, however, that it is possible to obtain a much more uniform and reproduceable compactness of the particulate sample if the container or receptacle is vibrated while said sample of material is gradually introduced into the container or receptacle. The introduction of the sample may be continuous or intermittent.

Alternatively, the sample of particulate material may be compacted by exposing it to ultrasound when all of the sample has been placed within the container or receptacle, but preferably while the sample is being introduced into the container or receptacle.

In practice a sample to be measured is normally filled into the sample receiving container or receptacle so as to fill a predetermined volume thereof, for example the total volume. It may then be of importance for the measurement to be made that the total weight of the sample in the container or receptacle is determined, because in connection with the volume the said weight will give an indication of the bushel weight or compactness of the sample. According to the invention the weight of the sample may be determined on the basis of the natural vibrational frequency of the container or receptacle with said sample contained therein, because the natural frequency is dependent on the total vibrating mass or weight, i.e. the weight of the container and sample.

The present invention also provides an apparatus for determining at least one component of a sample of a particulate material, such as grain or seed, said apparatus comprising a vibratably mounted sample container or receptacle, vibratory means for vibrating said container or receptacle, means for generating an alternating electric field in said container or receptacle, and means for measuring a permittivity value of the content of said container or receptacle and for determining said component on the basis of said permittivity value.

BRIEF DESCRIPTION OF THE DRAWING

The invention will now be further described with reference to the drawings, wherein.

DESCRIPTION OF THE PREFERRED EMBODIMENTS

Figure 1:
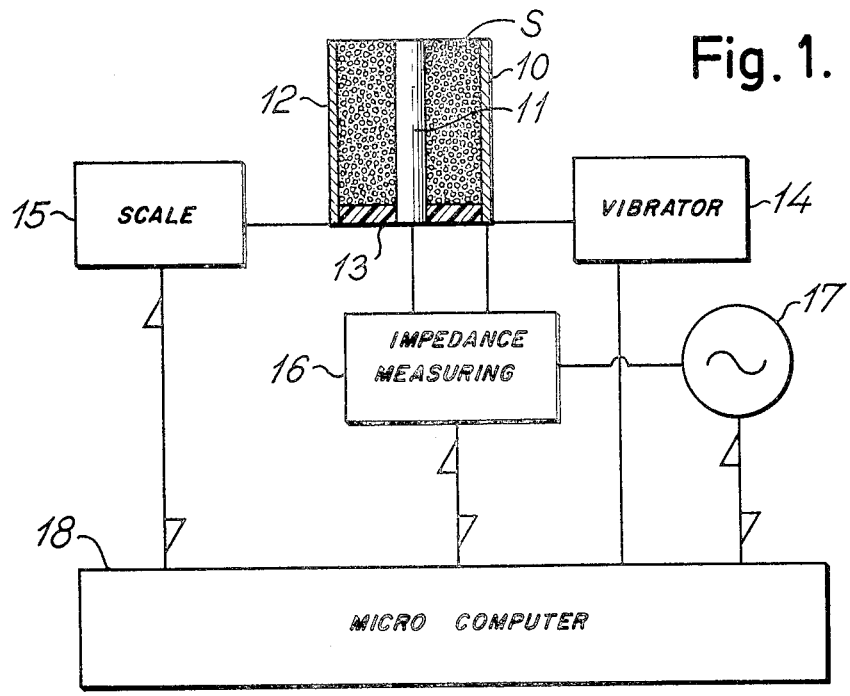
FIG. 1 is a block diagram of an embodiment of the apparatus according to the invention.

The apparatus of the invention comprises a sample receiving container or capacitor 10 in which a measuring chamber for receiving a sample S to be measured is defined between a central conductor or electrode 11 and an outer circumferential wall 12 forming the other conductor or electrode of the capacitor device. The conductors 11 and 12 are separated by an electrically insulating bottom wall 13. The capacitor or container 10 is connected to a vibrator 14 by means of which the sample S contained in the capacitor may be vibrated and compacted so as to obtain a reproduceable degree of filling. The capacitor 10 is also connected to a weight measuring device or scale 15 for measuring the weight of the sample S contained in the capacitor, and each of the conductors or electrodes 11 and 12 are connected to an impedance measuring device 16 which in turn is connected to a generator 17 for generating an alternating electric field between the conductors or electrodes 11 and 12. The vibrator 14, the weight measuring device 15, the impedance measuring device 16, and the generator 17 are each electrically connected to a control and calculating device 18, such as a microcomputer. This computer controls the operation of the various devices of the apparatus and calculates the content of one or more components in the sample S on the basis of the impedance or capacity measured by the device 16 when an alternating electric field is generated by the generator 17, of the weight measured by the device 15, and of empirical information stored in the memory of the computer 18.

Figure 2:
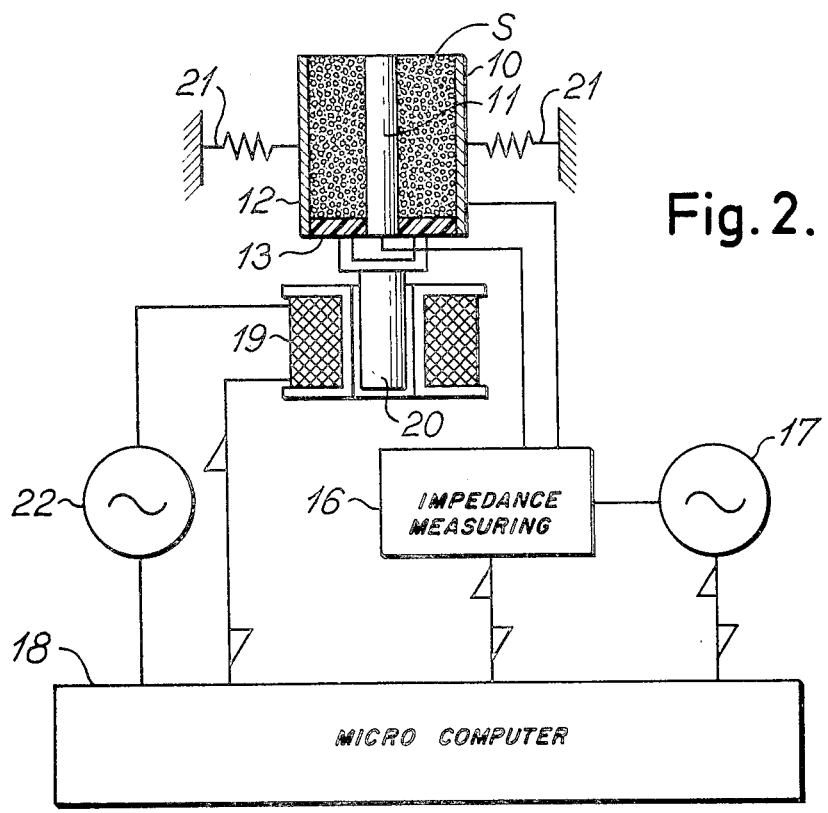
FIG. 2 is a diagrammatic illustration of part of a modified embodiment of the apparatus.

FIG. 2 shows a modified embodiment of the apparatus where the vibrator 14 and the weight measuring device are replaced by a solenoid 19 having a core 20. The container 10 is vibratably mounted as indicated by 21. The core 20 of the solenoid 19 is mounted on the insulating bottom wall 13 of the container or capacitor 10 while the solenoid 19 is stationary mounted. An alternating current may be supplied to the solenoid 19 by a generator 22, and the solenoid 19 as well as the generator 22 are connected to the computer 18 as shown.

When the apparatus shown in FIG. 2 is to be used, the generator 22 is energized so that it provides an AC-current to the solenoid 19 whereby the core 20 and consequently also the container or capacitor 10 are forcibly vibrated at a frequency determined by the frequency of the AC-current from the generator 22. While the container 10 is being vibrated the sample S is poured into the container 10 whereby the particles of the sample are uniformly compacted, and the container 10 is completely filled with the compacted sample. When the container 10 has been filled, the generator 22 is de-energized, and the container 10 with the core 20 will then for a short period of time continue to vibrate, but now with the natural vibrational frequency of the system. This natural vibrational frequency is dependent on the mass or weight of the container 10, the core 20, and the sample S as well as of the elastic properties of the container mounting means 21. It should be understood that the mass of the sample S is the only variable factor, and consequently, the natural vibrational frequency of the system is dependent on the mass or weight of the sample S. When the generator 22 has been de-energized, this natural frequency is detected by the solenoid 19, and a corresponding output signal is transmitted to the computer 18. The computer 18 then determines the weight of the sample S on the basis of that signal. In other respects the apparatus shown in FIG. 2 functions as described above in connection with FIG. 1.

It should be understood, that the principles of the present invention may be used in connection with any other apparatus for measuring one or more components of a sample of a particulate material on the basis of a permittivity value of the sample.

We claim:

1. A method of determining at least one component of a sample of a particulate material, such as grain or seed, said method comprising:
   introducing said sample in a movably mounted container,
   compacting said sample in said container to a predetermined degree by vibrating said container during the filling thereof with said sample,
   exposing said compacted sample in said container to an alternating electric field,
   measuring a permittivity value of said compacted sample,
   determining said component on the basis of said permittivity value, and
   determining the weight of the sample based on the natural vibrational frequency of said movably mounted container with said sample container therein.

2. A method according to claim 1, wherein said container is exposed to ultrasound to achieve vibration thereof.

* * * * *